United States Patent
Chong Rodriguez et al.

(10) Patent No.: US 11,122,688 B2
(45) Date of Patent: Sep. 14, 2021

(54) PADDED, FLEXIBLE ENCASING FOR BODY MONITORING SYSTEMS IN FABRICS

(71) Applicant: Bloomer Health Tech., Inc., Dover, DE (US)

(72) Inventors: Alicia Chong Rodriguez, Somerville, MA (US); Monica Lucia Abarca Abarca, Lima (PE); Aceil Halaby, Seattle, WA (US)

(73) Assignee: Bloomer Health Tech., Inc., Dover, DE (US)

( * ) Notice: Subject to any disclaimer, the term of this patent is extended or adjusted under 35 U.S.C. 154(b) by 41 days.

(21) Appl. No.: 16/665,669

(22) Filed: Oct. 28, 2019

(65) Prior Publication Data

US 2020/0128670 A1    Apr. 23, 2020

Related U.S. Application Data

(63) Continuation-in-part of application No. 15/642,583, filed on Jul. 6, 2017, now Pat. No. 10,456,080.
(Continued)

(51) Int. Cl.
*H05K 1/14*    (2006.01)
*A61B 5/0205*    (2006.01)
(Continued)

(52) U.S. Cl.
CPC ......... *H05K 1/145* (2013.01); *A61B 5/02055* (2013.01); *A61B 5/6804* (2013.01);
(Continued)

(58) Field of Classification Search
CPC .... H05K 1/145; H05K 1/0209; H05K 1/0272;
H05K 2201/0195; H05K 2201/0281; H05K 2201/10151; H05K 2201/10977; H05K 3/281; H05K 1/181; A61B 5/02055; A61B 5/6804; A61B 5/0022; A61B 5/4818;
(Continued)

(56) References Cited

U.S. PATENT DOCUMENTS 3,960,138 A * 6/1976 Doss ........................ A61B 5/01
                                                                           600/549
6,419,636 B1 * 7/2002 Young ..................... A61B 5/015
                                                                           600/372
(Continued)

*Primary Examiner* — Travis S Chambers
(74) *Attorney, Agent, or Firm* — Bachman & LaPointe, P.C.

(57) ABSTRACT

A wearable monitoring device comprising a printed circuit board having a first side and a second side opposite the first side, wherein the printed circuit board is configured to couple to at least one sensor configured to monitor a physiological condition; at least a first padding layer coupled to the printed circuit board proximate the first side; at least a second padding layer coupled to the printed circuit board proximate the second side; a first protective layer coupled to the first padding layer opposite the printed circuit board; a second protective layer coupled to the second padding layer opposite the printed circuit board; at least one additional layer between the first protective layer opposite the printed circuit board; the first protective layer and the second protective layer seal together and enclose the first and second padding and the printed circuit board; and a power source coupled to the printed circuit board.

24 Claims, 9 Drawing Sheets

Related U.S. Application Data

(60) Provisional application No. 62/501,826, filed on May 5, 2017.

(51) Int. Cl.
*H05K 1/02* (2006.01)
*A61B 5/00* (2006.01)

(52) U.S. Cl.
CPC ......... *H05K 1/0209* (2013.01); *H05K 1/0272* (2013.01); *H05K 2201/0195* (2013.01); *H05K 2201/0281* (2013.01); *H05K 2201/10151* (2013.01); *H05K 2201/10977* (2013.01)

(58) Field of Classification Search
CPC ... A61B 5/4088; A61B 5/4094; A61B 5/0816; A61B 5/318; A61B 5/0205; A61B 5/01; A61B 5/021; A61B 5/024; A61B 5/02405; A61B 5/6805
USPC ............................... 439/651, 37, 909; 2/905
See application file for complete search history.

(56) References Cited

U.S. PATENT DOCUMENTS

| | | | |
|---|---|---|---|
| 7,783,334 B2 * | 8/2010 | Nam | A61B 5/6805 |
| | | | 600/388 |
| 10,172,590 B2 * | 1/2019 | Nakamura | A61B 8/4477 |
| 2017/0367614 A1 * | 12/2017 | Zuckerman-Stark | |
| | | | A61B 5/0533 |

* cited by examiner

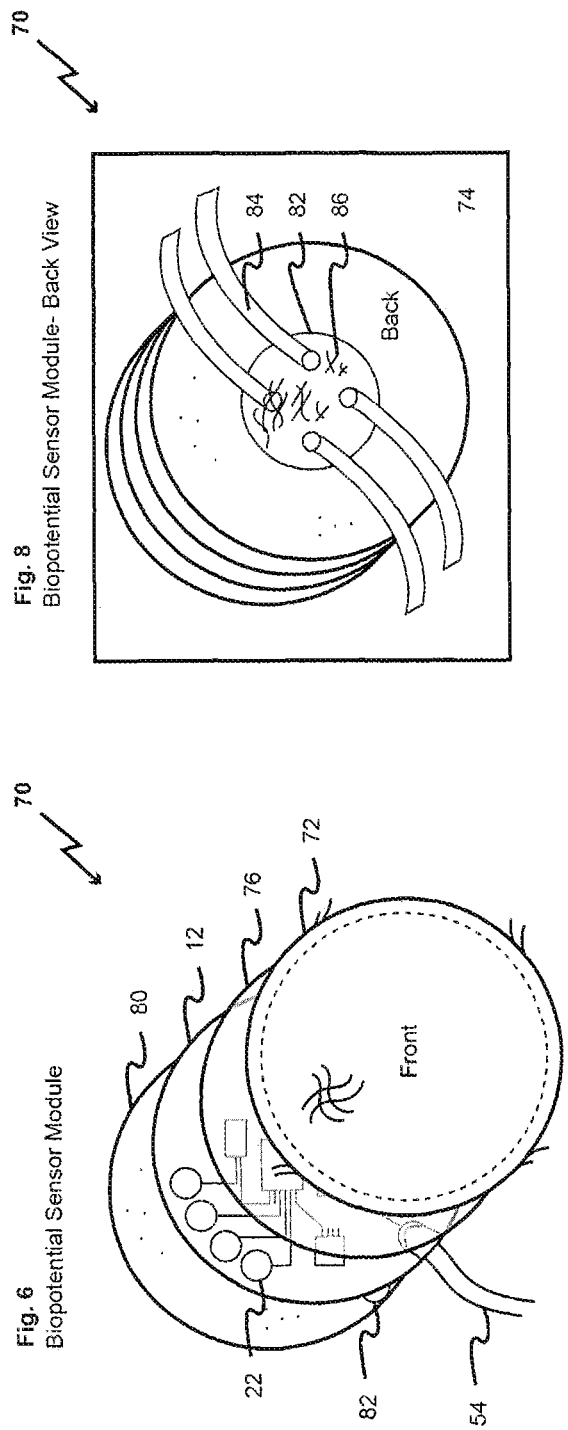
Fig. 6
Biopotential Sensor Module
Fig. 7
Biopotential Sensor Module- Cross Section
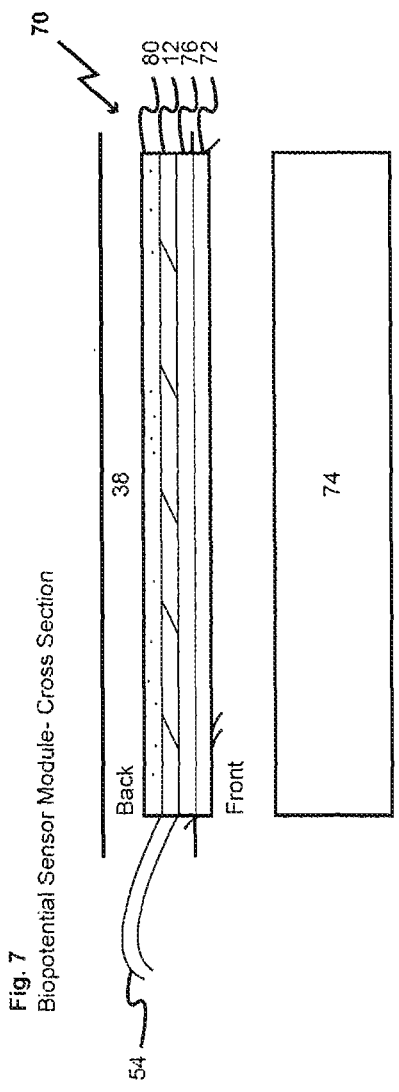
Fig. 8
Biopotential Sensor Module- Back View

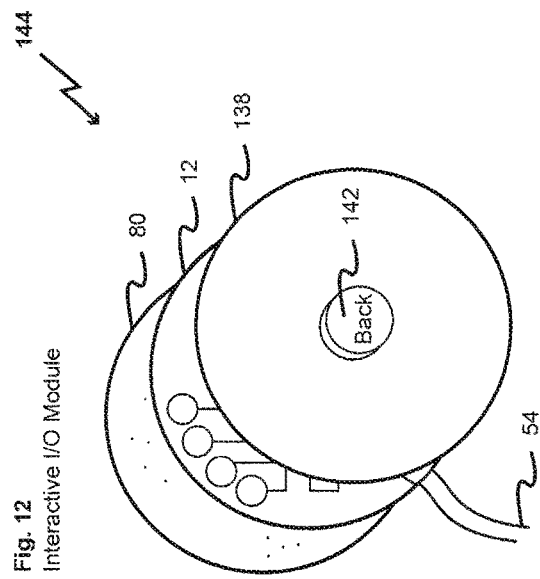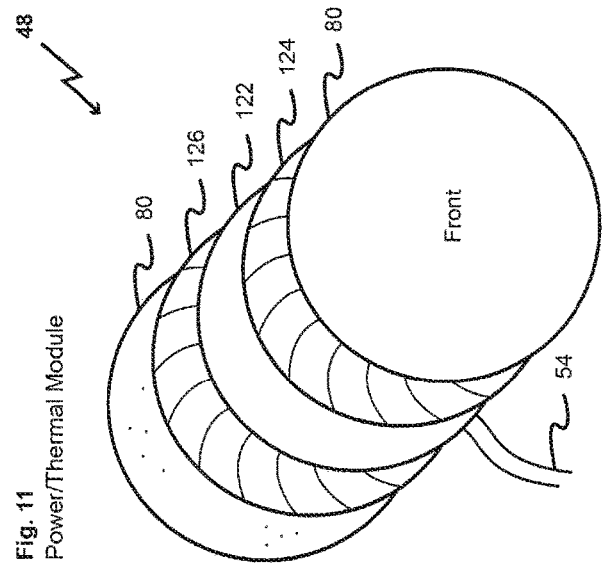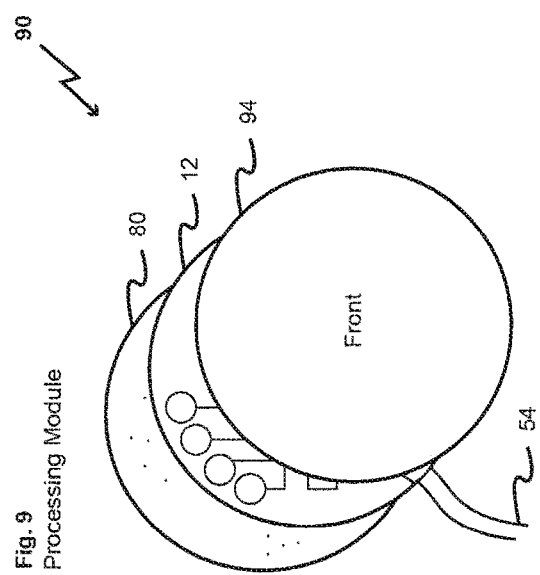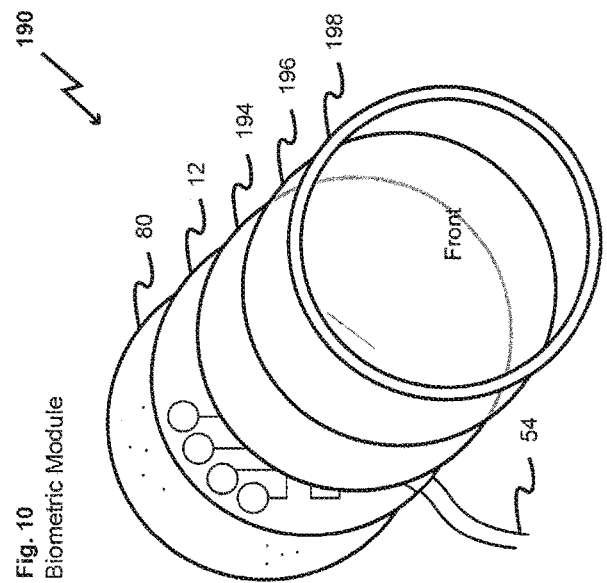

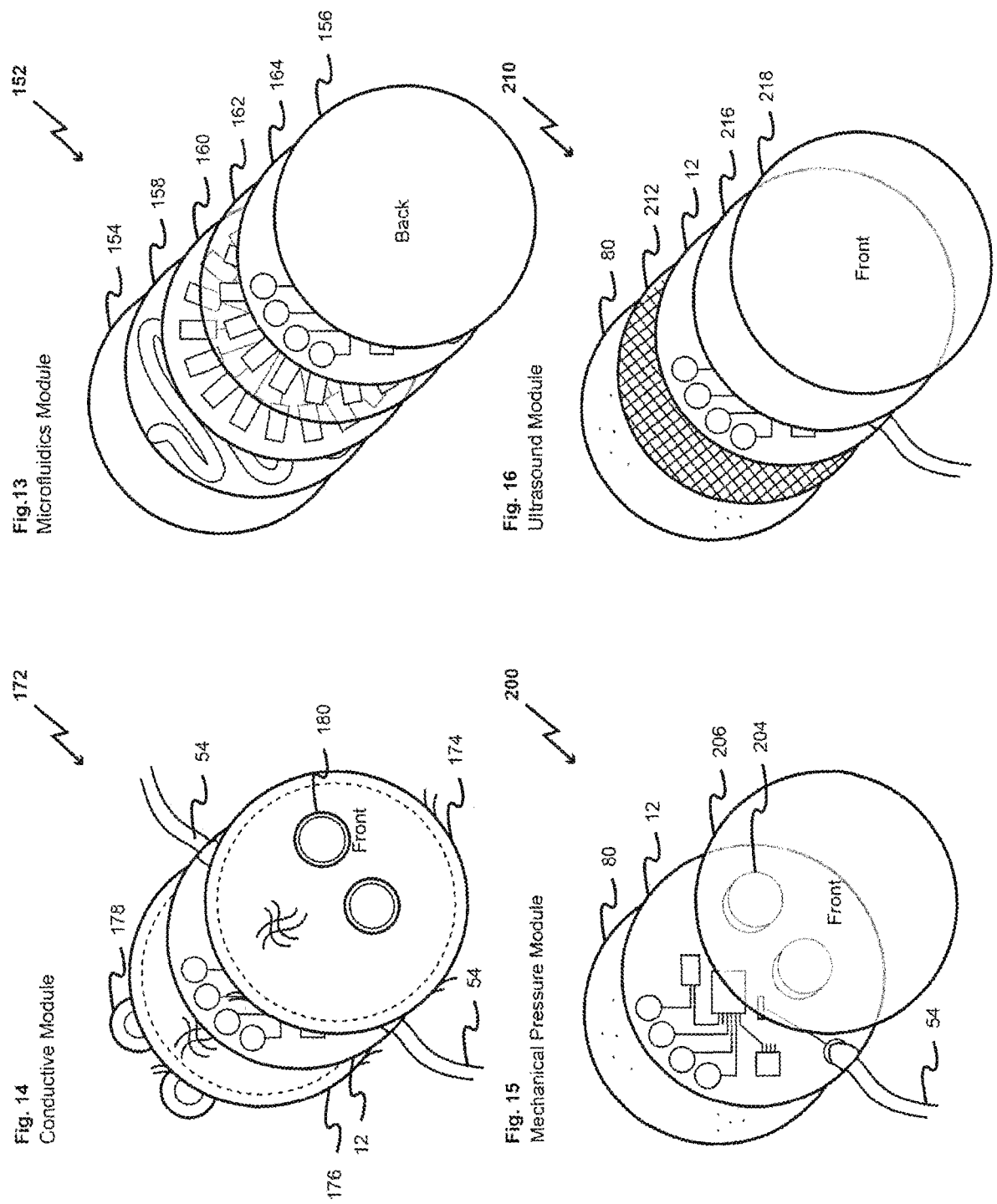

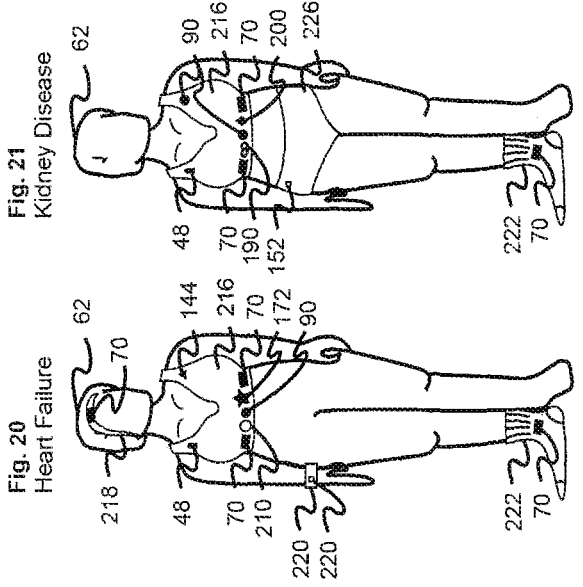
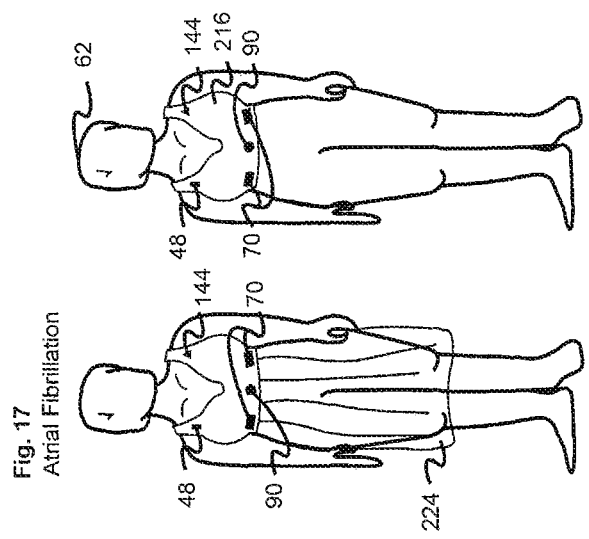
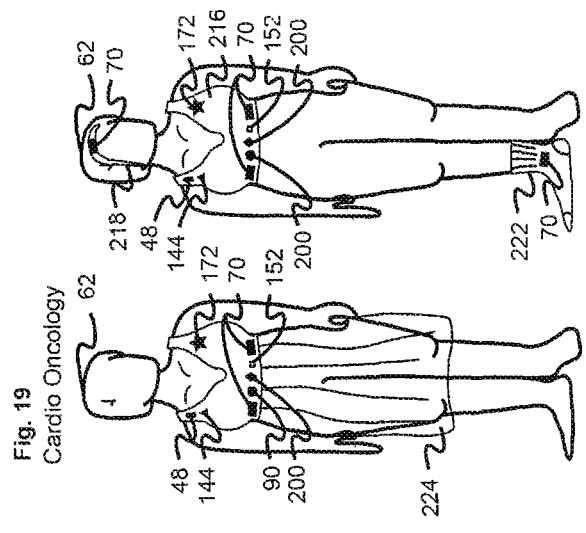
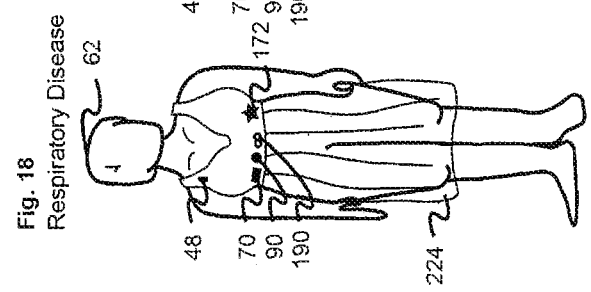

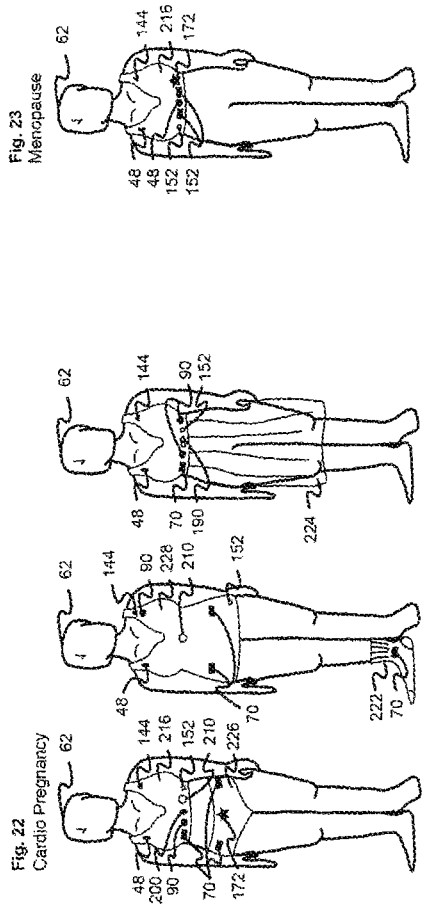

PADDED, FLEXIBLE ENCASING FOR BODY MONITORING SYSTEMS IN FABRICS

CROSS-REFERENCE TO RELATED APPLICATION

This application claims the benefit of U.S. Non-Provisional application Ser. No. 15/642,583, filed Jul. 6, 2017, issued as U.S. Pat. No. 10,456,080, which claims priority to Provisional Application Ser. No. 62/501,826, filed May 5, 2017.

BACKGROUND

The present disclosure is directed to a wearable monitoring device that is integrated into clothing and configured to detect and communicate measurements of a person's physiology.

Cardiovascular diseases cause more deaths globally than cancer, HIV and malaria combined. Infections, metabolic, respiratory and cardiac diseases, cancers and other illnesses are all massive problems that can be better tackled with continuous and event monitoring and personalized information of the patient for an efficient diagnosis.

Prior solutions include devices that can monitor certain body functions worn on the body. Those solutions attempt to address the issues of comfort and durability. Those past solutions include electronics that are bulky, stiff and uncomfortable. Typically, the batteries and microelectronics are stored in a hard case that is unyielding and difficult to integrate into clothing. Those systems are especially not easily integrated into clothing that is worn frequently, such as undergarments.

What is needed are clothes integrated with a comfortable device to obtain the status of the human body for prevention of cardiovascular diseases by tracking real time information of the heart to help deal with diseases and optimize health by making clothes intelligent and useful.

SUMMARY

In accordance with the present disclosure, there is provided a wearable monitoring device comprising a printed circuit board having a first side and a second side opposite the first side, wherein said printed circuit board is configured to couple to at least one sensor configured to monitor a physiological condition; a first padding layer coupled to said printed circuit board proximate the first side; a second padding layer coupled to said printed circuit board proximate the second side; a first protective layer coupled to said first padding layer opposite said printed circuit board; a second protective layer coupled to said second padding layer opposite said printed circuit board, said first protective layer and said second protective layer seal together and enclose said first and second padding and said printed circuit board; and a power source can be coupled to said printed circuit board.

In another and alternative embodiment, a garment having a wearable monitoring device comprising the wearable monitoring device coupled to said garment, wherein said wearable monitoring device comprises a printed circuit board having a first side and a second side opposite the first side, wherein said flexible printed circuit board comprises a microprocessor configured to process electrophysiological measurements and biometric measurements and wirelessly transmit said electrophysiological measurements and biometric measurements to another device selected from the group consisting of a computer, a mobile phone, a recording device and the like; a first padding layer coupled to said flexible printed circuit board proximate the first side; a second padding layer coupled to said printed circuit board proximate the second side; a first protective layer coupled to said first padding layer opposite said printed circuit board; a second protective layer coupled to said second padding layer opposite said printed circuit board, said first protective layer and said second protective layer sealing together and enclosing said first and second padding and said flexible printed circuit board; and at least one sensor coupled to said wearable monitoring device and said garment, said at least one sensor configured to monitor a physiological condition through inputs of said electrophysiological measurements and biometric measurements.

In another and alternative embodiment, a process for monitoring a physiological condition comprising donning a garment having a wearable monitoring device over a portion of a wearer's body, said wearable monitoring device comprising a printed circuit board having a first side and a second side opposite the first side; a first padding layer coupled to said printed circuit board proximate the first side; a second padding layer coupled to said printed circuit board proximate the second side; a first protective layer coupled to said first padding layer opposite said printed circuit board; a second protective layer coupled to said second padding layer opposite said printed circuit board, said first protective layer and said second protective layer sealing together and enclosing said first and second padding and said printed circuit board; a power source coupled to said printed circuit board; monitoring at least one physiological condition of said wearer with at least one sensor coupled to said wearable monitoring device and said garment; sending a signal including data of said physiological condition; and processing said signal and transmitting said signal to a collection device.

Other details of the wearable monitoring device are set forth in the following detailed description and the accompanying drawing wherein like reference numerals depict like elements.

BRIEF DESCRIPTION OF THE DRAWINGS

FIG. 6 is isometric view of an exemplary module.

FIG. 7 is a cross sectional illustration of the exemplary module of FIG. 6.

FIG. 8 is an isometric view of the exemplary module of FIG. 6.

FIG. 9 is an exploded isometric view of an exemplary processing module.

FIG. 10 is an exploded isometric view of an exemplary biometric module.

FIG. 11 is an exploded isometric view of an exemplary power management module.

FIG. 12 is an exploded isometric view of an exemplary interactive In/Out module.

FIG. 13 is an exploded isometric view of an exemplary microfluidic sensor module.

FIG. 14 is an exploded isometric view of an exemplary conductive module.

FIG. 15 is an exploded isometric view of an exemplary mechanical pressure module.

FIG. 16 is an exploded isometric view of an exemplary ultrasound module.

FIGS. 17-23 are schematic illustrations of exemplary garment and module combinations.

DETAILED DESCRIPTION

Figure 1:
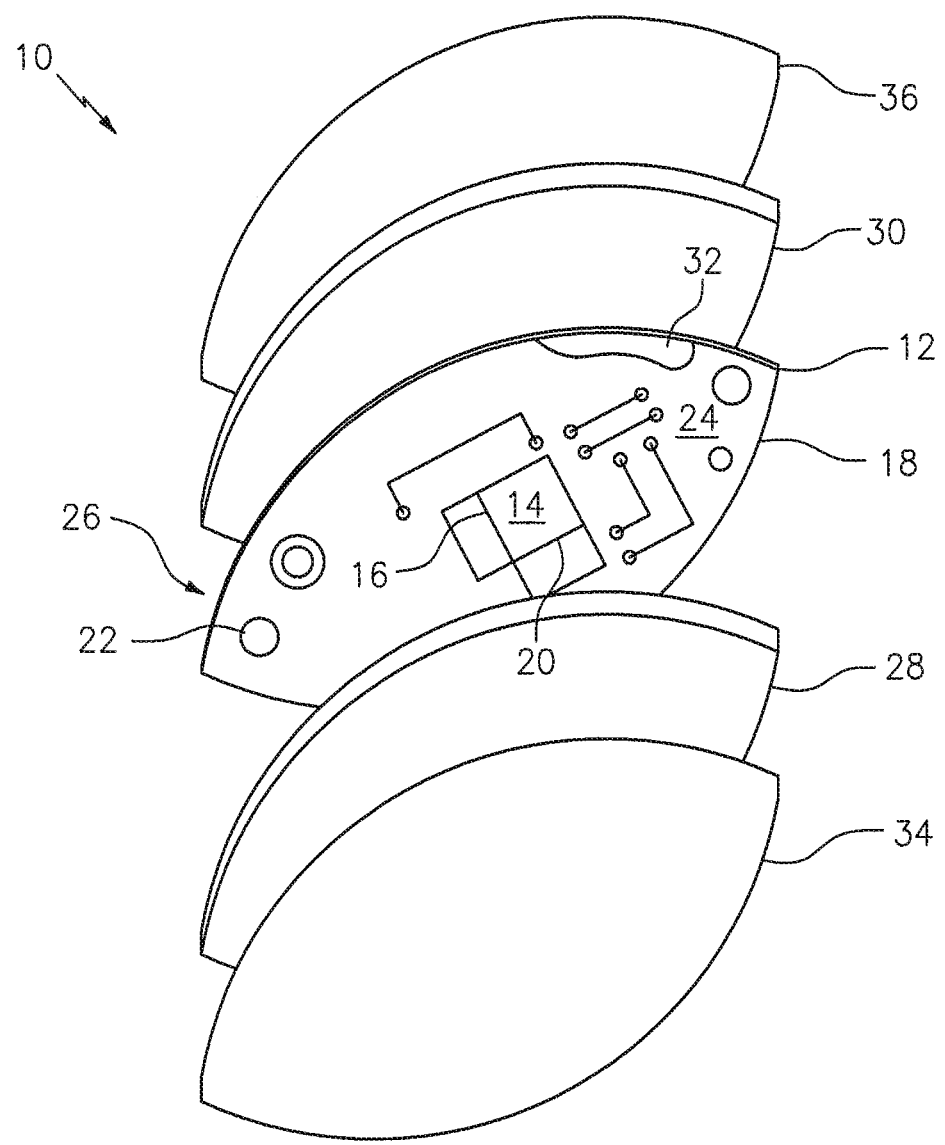
FIG. 1 is an exploded view of an exemplary wearable monitoring device.

Referring now to FIG. 1, there is illustrated an exploded view of an exemplary wearable monitoring device 10. The wearable monitoring device 10 comprises a printed circuit board 12. The printed circuit board 12 can include a processing unit 14 having at least one electronic component, e.g., microprocessor, 16 built into a substrate 18. A printed circuit board (PCB) mechanically supports and electrically connects electronic components using conductive tracks, pads and other features etched from copper sheets laminated onto a non-conductive substrate. Components (e.g. capacitors, resistors, integrated circuits or active devices) are generally soldered on the PCB. Advanced PCBs may contain components embedded in the substrate. The PCB can include, laminates, copper-clad laminates, resin impregnated B-stage cloth (Pre-preg), and copper foil. The printed circuit board 12 can be made of a flexible material or from a less flexible material or a rigid material. The printed circuit board 12 can include materials such as any kind Rigid PCB with a substrate such as a Flame Retardant, CEM, PTFE; a flex PCB (pyralux, Kapton, copper-clad foil or can be laminated to a thin stiffener) and the combination of both which can be a Rigid Flex. The processing unit 14 can comprise one or more processors 16, a memory 20, and input/output of electric or electronic signals 22. The printed circuit board 12 can include a first side 24 and a second side 26 opposite the first side 24

The printed circuit board 12 can be sandwiched between a first padding layer 28 coupled to said printed circuit board 12 proximate the first side 24. A second padding layer 30 can be coupled to the printed circuit board 12 proximate the second side 26. The first and second padding layers 28, 30 can be selected from the group consisting of foam, silicon, a material having a cellular structure resistant to electrostatic discharge (ESD) material (i.e., polyurethane), and memory foam, gelatinous material and poly laminate foam that protects the circuit board 12 from water and is comfortable and safe next to a body.

In an alternative embodiment, the printed circuit board 12 can include a thin film cover 32 that envelopes and protects the circuit board 12 from electrostatic discharge and water.

A first protective layer 34 can be coupled, bonded, laminated or layered to the first padding layer 28 opposite the printed circuit board 12. A second protective layer 36 can be coupled, bonded (i.e., tricot bonded), laminated or layered to the second padding layer 30 opposite the flexible printed circuit board 12. The first protective layer 34 and the second protective layer 36 are sealed together and enclose the first and second padding layers 28, 30 and the printed circuit board 12. The first protective layer 34 and the second protective layer 36 can be fabrics (i.e., waterproof polyurethane laminated (PUL) fabrics), soft advanced fabrics, hydrophobic material, and the like.

Figure 2:
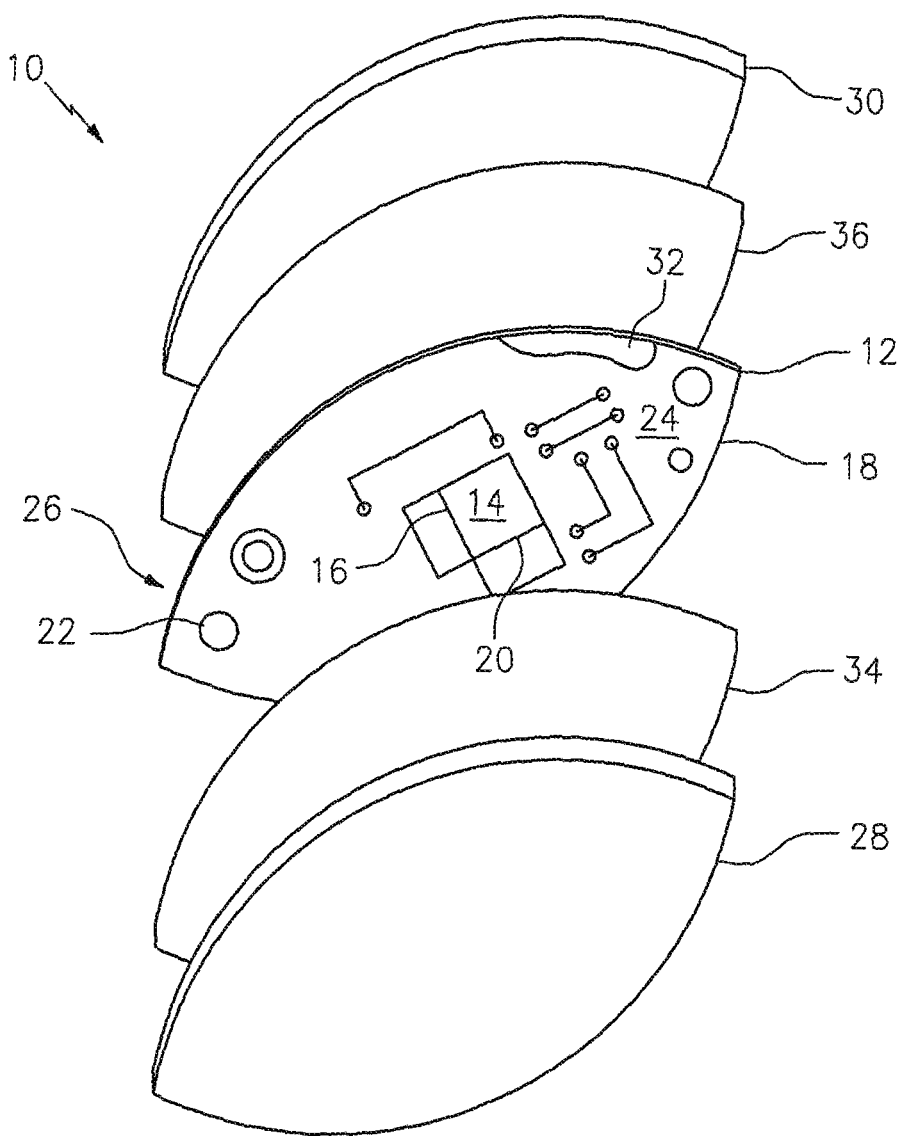
FIG. 2 is an exploded view of an exemplary wearable monitoring device.

In an alternative embodiment as shown in FIG. 2 the first protective layer 34 and second protective layer 36 can be placed closest to the printed circuit board 12. The first and second padding layers 28, 30 can be placed on against the first and second protective layers 34, 36 opposite the printed circuit board 12 respectively. The first and second protective layers 34, 36, can be coupled to the printed circuit board 12 to seal and protect the printed circuit board 12 from moisture and contaminants.

Figure 3:
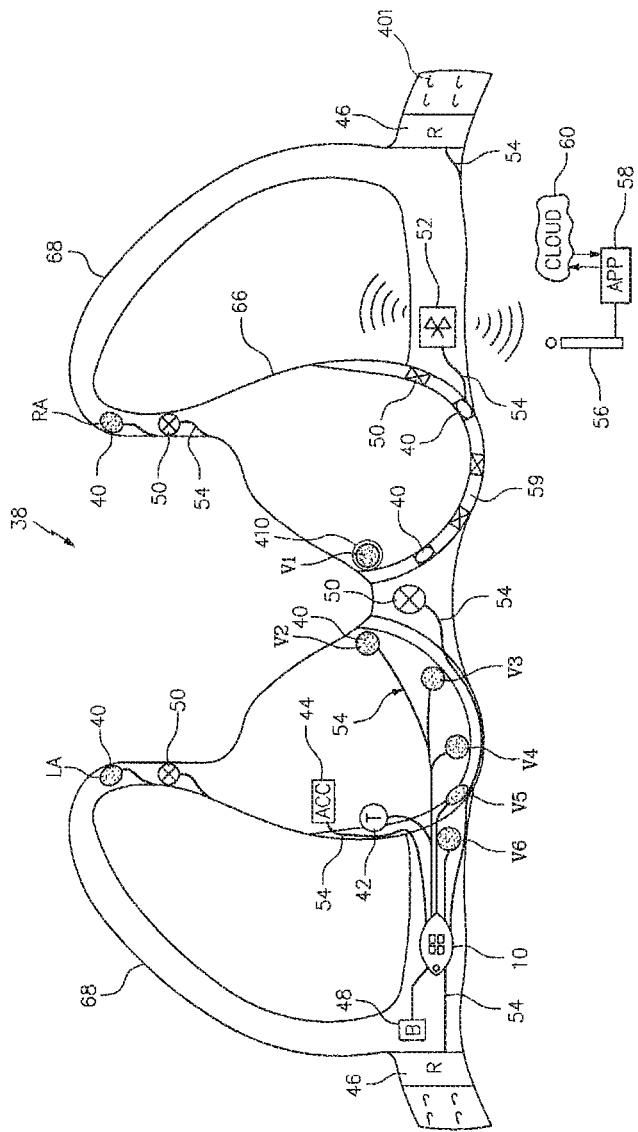
FIG. 3 is an illustration of a garment integrated with an exemplary wearable monitoring device and various sensors and transceiver.

The combination of the protective layers 34, 36 and padding layers 28, 30 surrounding the flexible printed circuit board 12 make up a uniquely wearable monitoring device 10 that can be easily integrated into a garment 38 as shown in FIG. 3.

The garment 38 is shown as an exemplary embodiment, as a bra and can also be any form of garment 38 that is used proximate the body, preferably the torso. Such examples of garments 38 include a brassiere, bustier, bra, corset, babydoll, bralette, basque, bodice torsolette, sports bra, panties, boxers, shirts, pants, jeans, jackets, sweaters, hats, socks and the like.

The garment 38 can include a variety of sensors such as soft-based modules 40 designed to sense a person's electrophysiology, biological features and the like. The sensors 40 can include at least one or more of the following: textile or fiber integrated sensors, acoustic sensors (i.e., Biometric module 190, Ultrasound Module 210), position sensors (i.e., processing module 90), optical sensors (i.e., Interactive I/O Module 144), piezo resistive sensors, temperature sensors (i.e., conductive module 172), electrocardiogram electrodes (i.e., biopotential modules 70), accelerometer (i.e., processing module 90), piezo resistive fabric, microphones (i.e., biometric module 190) and the like. The sensors 40 can be configured to obtain status of the human body for prevention, monitoring and treatment of diseases and health and aging status by tracking real time information of the heart, hereunder at least one or more of the following: heart rate, heart rate variability, heart rate recovery, electrocardiogram (in the following referred to as ECG), heart sound; lungs, hereunder at least one or more of the following: respiratory rate, minute ventilation, maximal oxygen consumption, lungs sounds; body metrics, at least one or more of temperature, movements, position, and the like.

The exemplary embodiment shown at FIG. 3 includes a variety of sensors 40, specifically a temperature sensor 42, an accelerometer 44, a piezo resistive sensor 46, electrophysiological sensors, V1, V2, V3, V4, V5, V6, LA, RA, RL, LL and the like.

A power source 48, such as a battery is shown coupled to the wearable monitoring device 10. The wearable monitoring device 10 can be coupled to the various sensors 40 and power source 48, switches 50, and wireless communicator or transceiver 52 by use of a conductor 54, such as conductive thread, wire and the like.

In addition to the sensors 40, the transceiver 52 can include, Wi-Fi™, BLUETOOTH™ wireless communication and/or other RF equipment wirelessly coupled to another transceiver 56, user interface, such as a smartphone 58, and cloud 60 and has the possibility of connecting to servers, computers, supercomputers or others for AI (artificial intelligence), machine learning and other data processing/interpreting methods. The data collected by the various sensors 40 can be processed by the microprocessor which can perform some low embedded machine learning algorithms 16 and transmitted by the transceiver 52 to transceiver 56 and shared through an application on the smartphone 58, displayed by using algorithms to provide valuable content.

The processing unit 16, the memory 20, the user interface 58, the one or more biometric sensors 40, and the input/output interface or conductive pad 22 may be communicatively connected via communications path(s). It is to be understood that some of these components may also be connected with one another indirectly. In some embodiments, components of FIG. 1 may be implemented as an external component communicatively linked to other internal components. For instance, in one embodiment, the memory 20 may be implemented as a memory on a secondary device such as a computer or smartphone that communicates with the device wirelessly or through wired connection via the I/O interface 22. In another embodiment. The user interface 58 may include some components on the device such as a switch 50, as well as components on a secondary device communicatively linked to the device via the I/O interface/conductive pad 22, such as a touch screen on a smart phone 58, or smart watch and the like. The raw data from the sensors 40 can pass through a processing stage that can include filters, operational and instrumental amplifiers and instrumental, analog to digital converters, analog front end and the like.

In another exemplary embodiment, the sensors 40 can be integrated with a bra wire casing 59. The bra wire casing 59 can include a textile material formed into a tube for receiving a bra wire (not shown) that is utilized to stiffen and support the garment 38. The sensors 40 and casing 59 can be integrated into a unit an integrated with the other sensors 40 of the garment 38.

Figure 4:
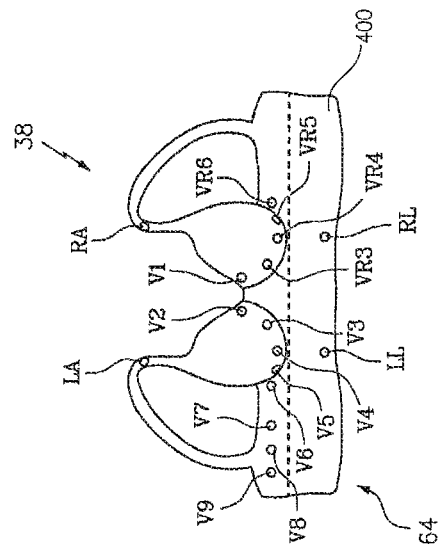
FIG. 4 is an illustration of an exemplary wearer.
Figure 5:
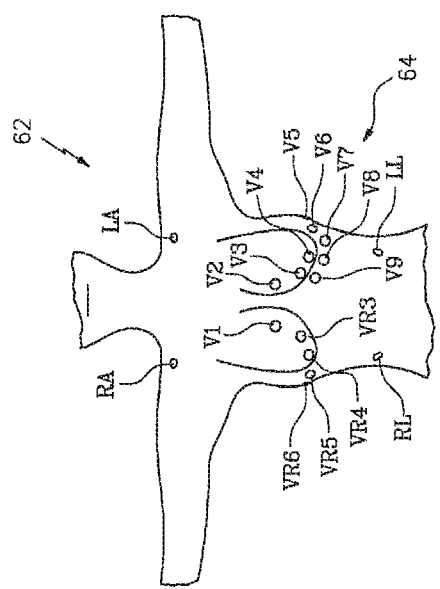
FIG. 5 is an illustration of an exemplary garment.

FIG. 4 and FIG. 5 illustrate a wearer 62 and the garment 38 and the variety of sensors 40 placed in locations 64 understood to be optimal for biopotential measurements of the cardiovascular system of the body. For biopotential measurements can be performed, minimum with two or more sensors/modules 40. The first pair of modules 40 will be on the same body axis at symmetrical ends such as LA and RA which are symmetrical or LL and RL are symmetrical too, then every additional biopotential sensor module can be placed individually such as V1-V9 and VR1-VR6 on a different axis of the heart. Similar configurations can be symmetrical to the brain, lungs or other organ or muscle being measured. The American Heart Association (AHA) and International Electrotechnical Commission include electrode positions for electrocardiogram or other cardiovascular measurements. The garment 38 can include sensor 40 locations following these guidelines.

The electrode positions (AHA lead wire labels/IEC labels, and the drawings are shown with AHA labels).

Electrode positions are commonly known as follows:
RA/R: Middle to outside end of the right clavicle, close to the bone;
LA/L: Middle to outside end of the left clavicle, close to the bone;
RL/N: Lower right trunk, just above the hip;
LL/F: Lower left trunk, just above the hip;
V1/C1: $4^{th}$ intercostal space at right border of the sternum;
V2/C2: $4^{th}$ intercostal space at left border of the sternum;
V3/C3: midway between V2 and V4;
V4/C4: $5^{th}$ intercostal space at midclavicular line;
V5/C5: level with V4 at left anterior axillary line;
V6/C6: level with V4-V5 at left midaxillary line;
V3R/C3R: midway between V1 and V4R;
V4R/C4R: $5^{th}$ intercostal space, right midclavicular line;
V5R/C5R: level with V4R at right anterior axillary line;
V7/C7: level with V4R at right anterior axillary line;
V8/C8: level with V4-V6 at left midscapular line;
V9/C9: level with V4-V6 at left spinal border.

Different electrode positions can be used to make measurements of the electrocardiogram different leads such as follows:

Bipolar limb leads (frontal plane):
Lead 1: RA (−) to LA (+) (Right Left, or lateral).
Lead II: RA (−) to LL (+) (Superior Inferior).
Lead Ill: LA (−) to LL (+) (Superior Inferior).
Augmented unipolar limb leads (frontal plane):
Lead aVR: RA (+) to [LA & LL] (−) (Rightward).
Lead aVL: LA (+) to [RA & LL] (−) (Leftward).
Lead aVF: LL (+) to [RA & LA] (−) (Inferior).
Unipolar(+) chest leads (horizontal plane):
Leads V1, V2, and V3: (Posterior Anterior).
Leads V4, VS, and V6: (Right Left, or lateral.

The wearable monitoring device 10 can be inserted in the brassier in a cup 66, the device 10 can be removable (from a pocket of thin textile) and/or sewn or embedded in the cup 66 itself, options will be available, the first and second protective layer 34, 36 can be replaced by a similar feeling textile with the device 10 inside, connected to two electrodes 40 in diverse positions. In another exemplary embodiment, the wearable monitoring device 10 can comprise the entire cup 66 as a single unit. The entire cup 66 with device 10 can be removable, integrated or a stand-alone unit.

There are many configurations of single-lead electrodes near the chest area, that covers all the positions of the recent ecg patches can be placed at (such as delta epatch, mc10, and other patches for arrythmias) the wearable monitoring device can have positions as above and can be inserted in the brassiere as part of the garment 38.

This monitoring device can be used for the inner-lining of padded bras and as cup input, replacement or complement, its padding component can come in many ranges of thickness, if padding is thick enough the flexible printed circuit board can be changed for a regular printed circuit board, as long as it is still not noticeable to the user and comfortable. A Single-lead configuration can include any two electrodes in different electrode positions (i.e., LA and RA).

In an alternative embodiment, the flexible circuit board 12 can be located under the arm, on the side of the bra 38 (left or right), or in the cup 66 or in the back. The flexible circuit board 12 is removable from a pocket and/or sewn. Several multiple lead configurations are available, including some or all of the lead-placements (also could be referred to as the combination of two or more diverse single-lead positions mentioned above).

In an alternative embodiment, the switches 50 can be configured as mechanical push button, touch sensor, and the like (round or square or other shape) and placed in 1, 2 and/or 3 strategic places:
a. 1 switch 50: in the mid-center of the bra 38 or on the left or right side of a bra strap 68 and the cup 66.
b. 2 switches 50: mid-center of the bra 38 and either the left or right side of the bra strap 68 and the cup 66 or left and right sides of the bra strap 68 and the cup 66.
c. 3 switches 50: mid-center of the bra 38 and left and right sides of the bra strap 68 and the cup 66.

In an alternative embodiment, the multiple switches 50 can be utilized as follows:
When in a 24-hour ECG Monitoring process (continuous monitoring): when the switch 50 is pushed by the wearer the device 10 stores the set of data in special format (flags/tags) the next flow of data from the heart and other sensors 40 for a time frame of at least 30 seconds to maximum 10 minutes depending on wearer's preferences, therefore if they feel a symptom or need to share a specific moment the data is tagged by use of the switch 50 and saved as priority automatically after pushing the switch 50 without opening an application or the need of any additional devices beyond the bra 38 itself.

Resting ECG: The wearer 62 lies down or gets into a resting position (i.e., seated) and pushes the switch 50 while a recording is made for a time frame of at least 30 seconds to maximum 2 minutes, depending on wearer's profile preferences.

Stress ECG: The user exercises either on a treadmill machine or bicycle and pushes the switch 50 and records for a time frame of at least 30 seconds to maximum 30 minutes depending on user preferences.

Event ECG: During non-continuous monitoring, the wearer 62 presses a direct record switch 50 and the device 10 records and stores the heart's electrical activity taking events at different moments at any part of the wearer's day for a time frame of at least 30 seconds to maximum 2 minutes depending on preferences and quantity of pushes during an event.

Event Recorder+Direct communication: During non-continuous monitoring, the wearer 62 presses a direct record switch and the device 10 records and stores the heart's electrical activity. The information can be sent to the physician or caregiver over the cloud 60 immediately.

The wearable monitoring device 10 can be utilized to obtain status of the human body for prevention and monitoring of cardiovascular diseases by tracking real time information of the heart, hereunder at least one or more of the following: heart rate, heart rate variability, heart rate recovery, electrocardiogram (in the following referred to as ECG), heart sound; lungs, hereunder at least one or more of the following: respiratory rate, minute ventilation, maximal oxygen consumption, lungs sounds; body metrics, hereunder at least one or more of the following: temperature, movements, position.

The wearable monitoring device 10 is configured to improve the measurements of the human body done through sensors, hereunder at least one or more of the following: textile or fabrics integrated sensors, acoustic sensors, position sensors, optical sensors, piezo resistive sensor, temperature sensor. The sensors are connected to protected circuits hereunder at least one or more of the following: protected circuit boards, flexible, semi rigid or rigid printed circuit boards. The sensors and the protected circuits will be placed seamlessly within clothes.

Referring to FIGS. 6, 7 and 8 an exemplary bio potential sensor module 70 is shown. The padding layer 80 can have similar properties to the above disclosed padding layers 28, 30. The padding layer 80 can include materials such as, foam, gelatinous material, silicon, and polylaminate foam. The padding layer 80 can also be layer 30 and 36 already coupled to each other, similarly to layer 28 and layer 24 already coupled to each other. Front of padding layer 80 is the printed circuit board 12 and back of padding layer 80 is garment 38. The back of padding layer 80 is configured to be attached directly to the garment 38 (see FIG. 3). The back of padding layer 80 can be a fabric, cloth material that can receive stitching, adhesives, and the like for attachment to the garment 38. As disclosed in detail above, the garment 38 can include but is not limited to an extension of a bra, interior of a tee shirt, a sock, underwear, hat, head band, and the like. In an exemplary embodiment of the sensor module 70, the interior of the garment 38 is needed to support the sensor module 70 so that the front 72 can contact the skin of the wearer 62. The bio potential sensor module 70 includes a fabric layer 72 which is configured to directly contact the skin 74. The fabric layer 72 is conductive can be hydrophobic and can have a tenacious grip to the skin 74. A conductive tape, or doubled sided adhesive 76 configured to conduct data sensed in the skin 74. A printed circuit board, flexible printed circuit board, thin film with conductive material, textile with conductive ink or similar or simply circuit layer 12 is coupled to the conductive tape 76, Circuit layer 12 has a conductive pad 22 to connect through the conductive adhesive 76 to the conductive fabric 72 to the skin 74. The conductive pad 22 in circuit layer 12 is important for the right signal acquisition from the body, therefore the pad is of highly conductive material (i.e., Ag/AgCl, immersion Gold, Silver or similar conductivity) should at least be sized enough to solder or connect to a wire, in other words the conductive pad 22 width: >150% of wire 54 diameter. The smaller this conductive pad 22 the bigger the conductive fabric size in layer 72 can be. The conductive pad can also be wireless, requiring the pad to be bigger size, the pad can have any shape any combinations of size and shape can be used as long as they have the proportional distribution that conductive fabric size area in layer 72 is much bigger when conductive pad 22 size area in layer 12 is smaller and the bigger the conductive pad 22 area in layer 12, the smaller the conductive fabric area size can be in layer 72. With the smallest size of the conductive pad 22 being that of a wire pad.

A padding layer 80, which can consist of a combination of padding layers 30 and 28 and protective layers 36 and 34, covers the printed circuit board 12 opposite the conductive tape 76. An opening 82 can be formed in the padding layer 80 to provide access for conductive leads or wires, connectors 54 to couple with layer 12, 78 through the padding layer 80. A sealing material can be utilized to seal the padding layer 80 around the conductive leads, wires, connectors 54 to protect layer 12, 78. The sealing material can be waterproof. Although the bio potential sensor module 70 is shown with conductive leads 54 configured to transmit electrical signals from the layer 12, 78, a wireless transmitter can be utilized instead of the conductive leads 54. Although opening 82 is shown, there can be no opening and the sealing is through lamination or similar and sealing material 54 can be on top of layer 80.

As seen in FIG. 8, module 70, biopotential modules can be active or inactive. Active means that layer 12, 78 can consist of a pcb (printed circuit board, flexible printed circuit board, fabric with conductive ink, thin film and the like) with electrical components such as an integrated circuits, operational amplifier, resistors, capacitors and similar filter and amplifier configurations on the side that is next to layer 80, this side would have a wire pad 54 to connect the output to other modules or would transmit this output wirelessly, by adding an rf antenna or similar and microcontroller, it can also have two additional wires 54 for power and ground sources or have a small battery prior to layer 80 for wireless. Inactive biopotential modules would not have the aforementioned electrical components, it would only have a wire pad 54 on either side of the layer, besides the larger conductive pad 22 that is next to layer 76 and connects to conductive fabric 72, if this fabric is bigger sized, then the wire pad would be only the wire soldered, attached or coupled to the side, else if the conductive fabric is more similar size to the pad size, the wire can be on a connected pad on the other side of the layer 12, 78, next to layer 76. If the inactive module is wireless, the side of 12, 78 next to layer 80 will have an rf antenna, microcontroller and power source.

The biopotential sensor module 70 usually is sewn, glued, attached in the garments in pairs, which means that they are placed in symmetrical positions of the body (i.e.; left and right arms, left and right side of the neck, legs, top or bottom, and the like). Together they measure biopotential differences. An individual biopotential sensor can be used when there is at least one or more pairs are already placed, therefore the third single 70 module can measure the biopotential differences with the result obtained by the other multiple 70 sensors. To obtain such measurements from the body, in mV or other unit, the embodiment needs to be touching the skin 74, this means the garment needs to be tight enough so that the module touches the skin 74. One side (the non-conductive side) 80 of the module is sewn, stitched, glued, attached or similar in the inner side of the garment and the other side (conductive side) 72 of the module will be touching the skin when the garment is worn by the wearer 62. The biopotential modules can do measurements of the body such as plethysmography, electrocardiography (ECG), impedance cardiography (ICG), Electroencephalogram (EEG), Electromyography (EMG), impedance, resistance and potential differences and others.

Referring to FIG. 9 an exemplary processing module 90 is shown. The processing module 90 can include an integrated circuit like a microcontroller, accelerometer, memory, application specific integrated circuit (ASIC), analog front end (AFE) or other in layer 12 between a front layer 94 and back layer 96. A conductor 54 can be coupled to the processor layer 92 configured to transmit signals, power and the like. The processor module 90 can be configured to store data, send and receive data from sensor modules, quickly analyze data in real-time and transmit information regarding the wearer 62. Understand the wearer 62 posture, movement, resting, activity, fall detection and similar analysis with their coordinates according to the location where placed on the body as well like the back, front or any of their joints. Other embodiments of this module are described above.

FIG. 10 exemplary textile-based biometric sensor module 190. The biometric sensor module 190 can include a front layer 198 that can be waterproof. The front layer 198 is configured to touch the wearer's skin 74. The front layer 198 can be made of any heat dissipating material that can be shaped into a ring such as rubber or be textile-based to function as an acoustic diaphragm that can provide an auscultation area that connects to the second layer 196.

A second layer can be a membrane 196. The membrane layer 196 can be configured to absorb sound pressure waves originating in the body. The membrane layer 196 is mechanically coupled to the acoustic stethoscope layer 194. In an exemplary embodiment, the acoustic stethoscope layer 194 may be a stamped cavity made of metal or flexible conductive material, or soft or hard, reflective, nonporous material. The acoustic stethoscope could also be an ultrasonic sensor that absorbs sound pressure waves originating in the body. The acoustic stethoscope layer 194 can be configured to couple to a printed circuit board layer 12 and can include a wire or cable 54, printed ink, conductive thread and the like. The second side 112 opposite the first side 110 can receive an adhesive (not shown). A connector 54 can be coupled to the circuit 12.

A padded protective layer 80 can be coupled to the circuit layer 12 opposite the acoustic stethoscope layer 194. The back padding layer is configured to next in the lining of a garment such as 38. Data from this module is digitized and can be viewed as a phonogram that is obtained through soft-based sensors 40.

FIG. 11 shows an exemplary power or thermal module 48. The power management module 48 includes a battery and/or circuit layer 12 nested between a first layer that can be a heat sink 124 to dissipate or holds heat and second layer can also be a heat sink 126 to dissipate or hold heat. A front padding layer 80 and back padding layer 80 are located on either side of each of the heat sink layers 124, 126 sandwiching the front and back of the power module 48. The protective layers 80 can include a moisture or water resistant material that conforms to the power module 48 contours. In an exemplary embodiment, the protective layers 80, can include a shrink wrap material that can tightly conform with the contours and seal out moisture, water and contaminants. A connector or wire 54 can be coupled to the battery/circuit layer 122. The connector 54 can be utilized to provide electrical power to other modules in the garment 38 when the other modules don't have their own battery. This module can also be used to pull heat away from wearer 62 through layer 80 touching the skin or pull heat to wearer 62 through layer 80 by integrating the soft module via sleeves, socks or around the torso.

FIG. 12 shows an exemplary interactive I/O module 144. The interactive I/O module 144, can be utilized as a switch or button, light emitting diode (LED) or photo plethysmography (PPG) or other optical sensor. The interactive I/O module 144 can include a back layer 138 of fabric, foam, gelatinous material, silicon and/or polylaminate foam configured to receive a switch, button and/or LED and/or optical sensor from 142. 142 can also be an input/output interface coupled to a circuit layer 12. In this module, back layer 80 is configured similarly to the front layer 138. The back layer 80 is configured to attach to the garment 38. A connector 54 can be coupled to the circuit layer 12 and provide connectivity to other modules on the garment 38. This module can be both in the inner side or outer side of the garment 38.

FIG. 13 shows an exemplary textiles-based microfluidic sensor module 152. The microfluidic sensor module 152 can include a front layer 154 of a foam, gelatinous material, silicon and/or polylaminate foam that is configured to contact the wearer's skin 74. The front layer 154 can be configured to attach to a one-way valve 158 to extract necessary fluids from the wearer's body. In an exemplary embodiment, the valve 158 can include a stainless steel, silicon and/or polylaminate foam. The valve 158 is configured to attach to a fluid tray 160. The fluid tray 160 is configured to store extracted body fluid for testing. In an exemplary embodiment, the fluid tray 160 can include soft, bendable materials or acrylic, glass, or similar material with an engraved path for fluid dynamics. The fluid tray 160 is configured so that it can eject from the module and be replaced and replaced with a new fluid tray that attaches to an air-channel 162. The air channel 162 is configured to store air that will allow body fluid stored in the fluid tray 160 to flow appropriately to the corners of the fluid tray 160 and be tested for health data interpretation. In an exemplary embodiment, the air channel 162 can include soft, bendable, silicon, acrylic, glass or similar material and precious metals and soft metals engraved with a mirrored path as the one in the fluid tray 160. The air channel 162 is configured to attach to a circuit layer 12. The circuit layer 12 is configured to interpret the health data from the air channel 162. A protective back layer 156 is configured to connect to the circuit layer 12, 164. A connector 54 can be coupled to the circuit layer 12 and provide connectivity to other modules on the garment 38. The shown microfluidic sensor module 152 can be detached from garments 38 and similar. Fluids that come from wearer 62 and go through this module 152 through the ejectable soft cartridges 162, 160 and 158 can include blood, urine, sweat and saliva. Garments that can have this modules include but are not limited to underwear, bra, t-shirts, socks, long-sleeves, gloves and forehead bands.

FIG. 14 shows an exemplary textile-based conductive sensor module 172. The conductive sensor module 172 can include a front layer 180 that is configured to contact the wearer's skin 74. In an exemplary embodiment the front layer 180 is made of a conductive textile 72, conductive non-allergenic materials or metal snap 180 that can consist of steel, Silver plated, high conductivity, Tin/copper coated, Cobalt alloy top coating, Silver (Ag) plated, Ag/AgCl silver/ silver chloride. The metal snap can have single, double or triple or more snap-style pellet configuration with fabric separation in between or have mix of conductive fabric with non-conductive fabric in between. The front layer 180 is adhered to a textile layer 174. In an exemplary embodiment the textile layer 174 can be made of organic or synthetic textile that is non-conductive. The textile layer 174 is coupled to a sealed, flexible printed circuit board layer, thin film or printed circuit board layer 12. The sealed 12 is coupled to another textile layer 176. In an exemplary embodiment, this second textile layer 176 is similar to layer 174 in that it can be made of organic or synthetic non-conductive textile. The back layer 178 can be the complementary half of the front layer 180, this module can also have 178 between circuit layer 12 and layer 176 and in another embodiment may not have layer 178, making 176 the back layer. In an exemplary embodiment the back layer can consist of the female or male half of the snap that completes the front layer 180. The textile layers 174 and 176 can be used to adhere the module to the garment by sewing, bonding or similar apparel manufacturing techniques.

Layer 182 is a flexible pcb, thin film, fabric with conductive printed ink, silver, gold, copper or the like where one side has the adhesive to the front layer and the other side has wires, cables, printed ink fabric, conductive threads or other type of connectors that will be longer and connect to another module such as the processing module or can be wireless and transmit the data captured. This layer can also have other integrated circuits or passive components soldered, sewn or glued.

Layer 176 can be a padding layer consisting of foam, gelatinous material, silicon and polylaminate foam.

Layer 176 can also be a combination of padding and fabric or just a fabric, cloth, sewable or glueable material that will be attached to the garment, such as an extension of a bra, interior of a t-shirt, interior of a sock, interior of underwear, hats and the like. This can only be placed in the interior of the garment.

FIG. 15 shows an exemplary mechanical pressure sensor module 200. The mechanical pressure sensor module 200 can include a front layer 206. In an exemplary embodiment the front layer 206 can be made of a perforated siliconized textile piezo-resistive fabric, a substrate or similar. The front layer is configured to adhere to the wearer's skin 74. On the opposite side, the front layer is configured to a piezoelectric layer 204. The piezoelectric layer 204 can be configured to send to and absorb sound pressure waves from the wearer 62. In an exemplary embodiment, the piezoelectric layer can be made of a substrate with polyamide, cu electrode, Cu/Sn electrode, piezo pillars, and epoxy filling and similar. The piezoelectric layer 204 is coupled to the printed circuit layer 12. The printed circuit layer 12 can have a wire 54 that connects the mechanical pressure module 200 to other modules 40 in the garment 38. The printed circuit layer is coupled on the other side to a back layer 80.

FIG. 16 shows an exemplary ultrasound sensor module 210. The ultrasound sensor module 210 can include a front layer 218. The front layer 218 is configured to adhere to the wearer's skin 74. In an exemplary embodiment, the front layer 218 can be made of a protective polymer or similar that is configured as an acoustic lens. The front layer 218 is coupled to a second, similar acoustic layer 216. The second acoustic layer is coupled with a printed circuit 12 that can have a connecting wire 54. The printed circuit 12 is coupled to a backing or acoustic insulating layer 212. In exemplary embodiment, the acoustic insulating layer 212 can be made of plastic, rubber, silicon or other materials to control acoustic attenuation. The acoustic insulating layer 212 is configured to adhere to a back layer 80 that nests within the lining of garment 38.

Referring also to FIGS. 17-23 schematic illustrations of exemplary garment and module combinations are shown. The exemplary garment and module combinations are for disclosure purposes, so it is contemplated that other combinations of modules and garments can be claimed. It is contemplated that various combinations of modules disclosed herein can be arranged on garments and located at beneficial positions relative to the wearer so as to provide optimal monitoring of the wearer for a host of symptoms and diseases and chronic conditions such as, but not limited to, epilepsy, Alzheimer's, hormone therapy, obesity, type 1 diabetes, type 2 diabetes, smoking, hypertension, genetic predisposal to heart disease or heart conditions, aging-related diseases and conditions, endometriosis, septicemia, depression, pulmonary embolism, ischemia, sleep apnea etc. Module combinations in exemplary garments can also be used to screen for the latter diseases and conditions.

The Atrial Fibrillation (Afib) illustration at FIG. 17, shows a wearer 62 with a garment 38 equipped with a variety of sensors 40 to detect, monitor, treat and manage Afib or stroke recurrence prevention via data from the sensor modules that get sent to the phone, and analyzed and can be provided to physicians and wearers. The sensors 40 can be coupled to the garment 38 based on a predetermined disease to provide input/output about the condition of the wearer 62. In the exemplary embodiment at FIG. 17, the garment includes at least two sensors 40. At least a pair of Bio-potential sensor modules 70 and one processing module 90. Other sensors can be added for additional monitoring of Afib and stroke prevention such as mechanical pressure 200, ultrasound modules 210, micro-fluidics module 152, interactive I/O modules 144, and power modules 48 can cooperate to provide more information for longer periods of time about the wearer 62. The FIG. 17 shows both a night gown 224 (e.g. night dress, night shirt, pajama top, tank top, tank top with sewn in chest support etc.) and a bra 216 (e.g. contour bras, wireless bras, t-shirt bras, push-up bras, demi and balconette bras, bralettes, convertible bras, strapless bras, sports bras, minimizer bras, stick-on bras, backless bras, surgical bras, nursing bras, bikini tops, training bras, swimsuits, bodys, shapewear and corsets) as examples.

Measurements performed by these modules include providing long-term monitoring capabilities of the wearer 62 can include but are not limited to asymptomatic and symptomatic electrocardiogram abnormality detection, continuous and event monitoring, weakness and fatigue, reduced ability to move or exercise, lightheadedness, dizziness, shortness of breath and respiration rate, chest pressure, pain or discomfort, stress or electrodermal response changes, blood tests, troponin tests. This also works well with the information of the wearer 62 stored in cloud 60 and the app 58 to provide an enhanced view and generate automated reports for the physician of the trends, changes and treatment impact of the wearer 62.

FIG. 20 shows a wearer 62 with garment 38 having a combination of predetermined sensors 40. To screen for, detect, manage and treat digitally the ailments of Heart Failure. Wearers 62 are patients and physicians can collect data that can be further analyzed with algorithms from 2 or more modules depending on the level of risk or diagnosis for heart failure. In the exemplary embodiment of FIG. 17c data for heart failure can be collected from at least the following sensors 40: more than 3 Bio-potential sensor modules 70, processing modules 90 and may additionally have power module 48, biometric modules 190, micro-fluidics module 152, conductive modules 172, ultrasound modules 210 and interactive I/O modules 144 depending on the patient's needs. In an exemplary embodiment, up to 4 garments with sensors 40 can capture valuable data between day and night for heart failure patients or people at risk of heart failure, these garments can be worn as needed and can include underwear 226 (e.g. boy shorts, classic briefs, hipsters, thongs, French-cut panties, G-string, shapewear, control briefs, seamless, Brazilian brief, leak-proof underwear, cheeky underwear, high-cut briefs, jock straps, trunks, boxers, mid-way trunks etc.), pants, leggings, sleeves, arm tights, leg tights, shirt, bra 216, headband 218 (i.e. bands to hold hair down, as jewelry, or medical bands), wrist band 220 (e.g. watch, bracelet, wrist band, cuff etc.) and sock 222 (e.g. compression socks, no-show socks, liner socks, low-cut socks, athletic socks, quarter anklets, over-the-calf socks, mid-calf socks, pantyhose, toe covers, toe socks, toe shoes etc.). Measurements performed by these modules include providing long-term monitoring capabilities of the wearers 62 can include but are not limited to sudden weight gain, electrocardiogram, reduced ability to move or exercise, mental confusion, ankle swelling, abdominal pain, shortness of breath, increased fatigue, loss of appetite, coughing and wheezing, fluid buildup, blood tests, troponin tests, echocardiogram, hydration level, stress tests and others for corrective interventions, treatments and early detection as well as improved quality of life by understanding their disease stages better from day to day, minute to minute, second to second data collection.

FIG. 18 shows a wearer 62 with garment 38 having a combination of predetermined sensors 40. To screen for, detect, manage and treat digitally Respiratory Diseases, patients and physicians need to collect data from at least 1 processing module 90. Additional modules, depending on the level of risk for Respiratory Disease can be included. In the exemplary embodiment of FIG. 18 data for Respiratory Disease can be collected from the following sensors 40: Bio-potential sensor modules 70, conductive modules 172, biometric modules 190, processing modules 90, power module 48, ultrasound modules 210 and interactive I/O modules 144. In an exemplary embodiment, garments that capture the required data between day and night and as needed can include: the daily bra 216, and night dress/shirt 224. Measurements performed by these modules include providing short and long-term monitoring capabilities of the wearers 62 can include but are not limited to symptom tracking via impedance measurements, body temperature for cold, fever or flu, continuous and event electrocardiogram monitoring, weakness and fatigue, reduced ability to move or exercise, lightheadedness, dizziness, shortness of breath and respiration rate, congestive, phlegm discomfort, blood tests, spirometry tests, minute ventilation, maximal oxygen consumption, lungs sounds. This also works well with the information of the wearer 62 stored in cloud 60 and the app 58 to provide an enhanced view and generate automated reports for the physician of the trends, changes and treatment impact of the wearer 62.

FIG. 21 shows a wearer 62 with garment 38 having a combination of predetermined sensors 40. To screen for, and detect, manage and digitally treat Kidney Disease, patients and physicians need to collect data from at least a pair of biopotential modules 70 and more modules can be added depending on the level of risk for Kidney Disease. In the exemplary embodiment of FIG. 21 data for Kidney Disease can be collected from the following sensors 40: Bio-potential sensor modules 70, biometric modules 190, processing modules 90, power module 48, micro-fluidics module 152, conductive modules 172, mechanical-pressure module 172 and interactive I/O modules 144. In an exemplary embodiment, garments that capture the required data between day and night and as needed can include: the daily bra 216, underwear 226 and socks 222. Measurements performed by these modules include providing short and long-term monitoring capabilities of the wearers 62 can include but are not limited to mental sharpness, electrocardiograms, nausea, muscle twitching and cramps, vomiting, hydration level, swelling feet, fatigue and weakness, itching or allergies, fluid build-up, sleep disturbances and tracking, blood tests, urine tests and blood pressure. This also works well with the information of the wearer 62 stored in cloud 60 and the app 58 to provide an enhanced view and generate automated reports for the physician of the trends, changes and treatment impact of the wearer 62.

FIG. 23 shows a wearer 62 with garment 38 having a combination of predetermined sensors 40. To screen for, detect, control and manage menopause, reproductive cycles, fertility tracking and diseases like endometriosis wearers 62 will benefit from the data collected from at least the conductive module 172 with core body temperature or basal temperature sensing capabilities and more modules can be used depending on the stage for menopause or any other needs from the reproductive system. In the exemplary embodiment of FIG. 23 data for menopause, menarche, peri- and post-menopausal, reproductive cycle and can be collected or outputs to the wearer 62 from the following sensors 40: Bio-potential sensor modules 70, processing modules 90, thermal module 48, biometric modules 190, micro-fluidics module 152, ultrasound modules 210 and interactive I/O modules 144. In an exemplary embodiment, garments that capture the required data between day and night and as needed can include the daily bra 216.

Measurements performed by these modules include providing short and long-term monitoring capabilities of the wearers 62 can include but are not limited to hot flashes, electrocardiograms, night sweats, period cycle tracking, fertility window tracking, follicle-stimulating hormone test, other hormone tests, urine tests, gonadotropin test, muscle twitching and cramps, vomiting, hydration level, swelling feet, fatigue and weakness, pregnancy tests, fluid build-up, sleep disturbances and tracking and blood pressure. This also works well with the information of the wearer 62 stored in cloud 60 and the app 58 to provide an enhanced view and generate automated reports of the trends, changes and treatment impact of the wearer 62.

FIG. 19 shows a wearer 62 with garment 38 having a combination of predetermined sensors 40. To screen for, detect, diagnose control, manage and digitally treat oncology early detection, post-diagnosis or post-treatment and during remission of cancer and cardio-oncology to ensure the wearer 62 cardiovascular system of cancer patients and survivors that can have potential risk of developing heart conditions if patients take certain types of cancer drugs, or following radiation treatment to the chest. The wearer 62 will benefit from the data collected from at least a pair of bio potential sensor modules 70 with electrocardiogram sensing capabilities and more modules can be used depending on the risk level of the oncology or cardio-oncology related disease. In the exemplary embodiment of FIG. 19 data biological, physiological and other data can be collected from the following sensors 40: Bio-potential sensor modules 70, processing modules 90, power module 48, mechanical pressure modules 200, micro-fluidics module 152, conductive modules 172 and interactive I/O modules 144. In an exemplary embodiment, garments that capture the required data between day and night and as needed can include the daily bra 216, a night dress/shirt 224, a headband 218, and socks 222.

Measurements performed by these modules include providing short and long-term monitoring capabilities of the wearers 62 can include but are not limited to blood pressure, mental confusion, sudden weight gain, electrocardiogram, ankle swelling, abdominal pain, fever or headache, shortness of breath, increased fatigue, loss of appetite, coughing and wheezing, fluid build-up, insulin blood test, cholesterol blood test, other blood tests, ultrasound, heart imagine, blood clot detection, CT/MRI scan, echocardiogram, stress and hydration levels, cardiac toxic side effects from oncology treatment. This also works well with the information of the wearer 62 stored in cloud 60 and the app 58 to provide an enhanced view and generate automated reports for the physician of the trends, changes and treatment impact of the wearer 62.

FIG. 22 shows a wearer 62 with garment 38 having a combination of predetermined sensors 40. To screen for, detect, diagnose, control, manage and digitally treat cardio pregnancy, any risk of cardiovascular disease, blood clots or artery dissection or bursts while pregnant, or female reproductive health related diseases such as hyperlipidemia, gestational diabetes, preeclampsia and polycystic syndrome or hemorrhages. This monitoring device would serve to assess the wearer's 62 cardiovascular system does or does not have a potential risk of developing heart conditions upon ingesting certain drugs, or following body stresses or alternative treatments. The wearer 62 will benefit from the data collected from at least a pair of bio potential sensor modules 70 with electrocardiogram sensing capabilities and more modules depending on the risk level of the cardio-pregnancy or female reproductive system related disease. In the exemplary embodiment of FIG. 22 biological, physiological and other data can be collected from the following sensors 40: Bio-potential sensor modules 70, processing modules 90, power module 48, mechanical pressure modules 200, micro-fluidics module 152, conductive modules 172, biometric modules 190, ultrasound modules 210 and interactive I/O modules 144. In an exemplary embodiment, garments that capture the required data between day and night and as needed can include the daily bra 216, a night dress/shirt 224, a headband 218, a camisole 228 (e.g. camisole, shapewear, maternity belt, maternity band, belly band etc.) socks 222.

Measurements performed by these modules include providing short and long-term monitoring capabilities of the wearers 62 can include but are not limited to temperature changes, electrocardiograms for wearer 62 and electrocardiograms for fetus if she is pregnant, night sweats, period cycle tracking, weight gain, activity levels, cholesterol blood tests, triglycerides blood test, muscle twitching and cramps, vomiting, hydration level, swelling feet and ankles, fatigue and weakness, itching or allergies, fluid build-up, sleep disturbances and tracking, blood tests, anemia test, urine tests, Doppler ultrasound, snoring, insulin blood test, headaches, abnormal swelling in body parts including hands and face, electroencephalogram, fetal heart rate, fluid in the lungs, blood pressure, baby movement, baby activity, baby vital signs, contractions, monitoring repercussions of miscarriages, pregnancy stress on the organs, respiratory system, digestive tract, muscular system such as her abdominal, exercise response while pregnant, heart rate, heart rate variability. This also works well with the information of the wearer 62 stored in cloud 60 and the app 58 to provide an enhanced view and generate automated reports for the physician of the trends, changes and treatment impact of the wearer 62.

The advantages of the wearable monitoring device is to configure a bra with sensors and washable circuits, because it is located in the critical anatomical sections of the body allowing for monitoring of the heart, lungs and more. The bra will monitor critical health parameters of women, empowering them by providing information critical to their bodies. Since bras are worn daily, the wearable monitoring device will deliver valuable and meaningful, out of the care provider's office continuous and/or event based information of cardiac health, respiratory health and more, in a seamless and safe way.

Another advantage of the wearable monitoring device is that it comprises washable flexible padded encasing for circuits to be used in daily clothing, being an unnoticeable additional material attached to the daily clothing and keeping the comfort and utility of the daily clothing, by being seamless and not interfering with how the clothing is normally used.

The wearable monitoring device may be inserted into, removed from and sewn into a plurality of compatible garments (e.g., bralletes, brassieres, camisole tops). It can be easily integrated as padding, as the cup or a clothing component, sewn or removable, in garments. The device integrates into textiles, fabrics and clothing, it is soft flexible insertable and sewn, leaving behind the use of hard, bulky devices that are attached separately to garments.

This advanced device can be a cup of a bra, which is the fabric covering the breast of women. It can be integrated in a smooth way that is not noticeable to the user in a variety of bra types and coverage levels such as full coverage, a percentage of coverage (medium coverage), demi or balconette or others such as almond shape, eye, and or triangular shaped cups and even a flat squared or round shape.

This monitoring device can be used for the inner-lining of padded bras and as cup input, replacement or complement, its padding component can come in many ranges of thickness, if padding is thick enough the flexible printed circuit board can be changed for a regular printed circuit board, as long as it is still not noticeable to the user and comfortable.

The monitoring device has been designed to improve signal-to-noise ratio and reduce instrumental noise, acquire better signals from the body in regards to the sensor being used. Each module includes layers that increase their capacity to sense the physiological parameters to provide best data from each sensor type for data-driven monitoring and treatment of patients with different diseases. The devices include locations, materials and components to integrate seamlessly into an everyday garment so that noise is reduced and signal acquisition increased. Access to enable unique user experience by allocating the sensors in a place where it is comfortable for each unique body size, shape and form, obtains key parameters for their different diseases or health status and is invisible to their daily interaction with the garment, so no habit changes. Modular capacity of adding or removing modules into the garments depending on the long-term or short-term monitoring, treatment, disease diagnosis, detection and tracking is an advantage to tailor treatment and make it personal to each individual's needs and learning, via algorithms using the data collected from their body. Also the modular design aims to provide longer life cycle of the garment with wearable monitoring capabilities, as each module can have its own battery and be wireless or be interconnected and have optimal power management. It also enables reduction of electronic waste in smart garments by using layers that can be reused, replaced and transferred to other garments.

The monitoring device can have the shape of an adjustable extension 400 for a bra or a sensor fabric swatch for other garments 38 comprised of fabrics, elastic, lace material and the like that attaches, sews and adheres to couple with any existing garment 38 such as the design of a daily bra, brallete, sports bra, t-shirt bra, lingerie or similar top. This adjustable extension 400 becomes a component of a bra that is designed to match the bra pattern of any existing bra design so that the wings are the same length. Therefore, the adjustable extension 400 is coupled to an existing garment 38. A pair of complimentary adjustable connector/hooks 401 make the extension look like a single unit, essentially transforming any existing garment 38 or bra to a monitoring device by placing new hooks 401 to the existing bra that go over the bra extension as well. The adjustable bra extension 400 can have add-ons such as elastic and the connector/hooks 401 to make the bra extension tighter. When placed in the wearer 62 torso and when complimentary connector/hooks 401 are closed, electrically connected, hooked and the garment 38 is touching the wearer's body the wearable monitoring device is activated. When the connector/hooks 401 of the bra are open, electrically disconnected, unhooked and lose the device turns Power OFF. The adjustable extension 400 can be coupled to garment 38 solely from the connector/hooks 401. Having connector/hooks 401 in the extremities, the extension can go around the wearers torso or around other body parts one or multiple times to tighten, fasten the extension and connect to any garment 38 or bra with a connector/hooks 401. Comprising sensors 40, distributed along the locations for body measurements, once fastened with the adjustable connector/hooks 401 sensors 40 will be firmly touching against skin of the wearer 38. In an exemplary embodiment, a pad 410 can improve contact between the sensors 40 and skin and reduce movement of the sensors 40 on the skin. The pad 410 can comprise a stay-put washable and reusable silicone lining, a silicone band, silicone dots or any silicon pattern or Silica gel glue, and/or adhesive and the like placed around sensors 40. Combination of similar materials around the sensors 40 and throughout the adjustable extension 400 can be used as long as they will not cause irritation, redness, itching or other side effects. Using only non-allergenic materials to skin that allow friction so when the sensor that contacts the skin and is around the fabrics or lace top hugs the torso/chest or other part of the body of wearer 62 so that adjustable extension 400 stays put and noise to sensors 40 is reduced.

There has been provided a wearable monitoring device. While the wearable monitoring device has been described in the context of specific embodiments thereof, other unforeseen alternatives, modifications, and variations may become apparent to those skilled in the art having read the foregoing description. Accordingly, it is intended to embrace those alternatives, modifications, and variations which fall within the broad scope of the appended claims.

What is claimed is:

1. A wearable monitoring device comprising:
   a printed circuit board having a first side and a second side opposite the first side, wherein said printed circuit board is configured to couple to at least one sensor configured to monitor a physiological condition, wherein said at least one sensor is configured to take at least one of physiological measurements, biometric measurements, microfluidic measurements, mechanical pressure measurements, ultrasound measurements and biopotential measurements;
   at least one padding layer coupled to said printed circuit board proximate the first side;
   at least one protective layer coupled to said at least one padding layer opposite said printed circuit board;
   at least one additional layer coupled to said printed circuit board proximate said second side;
   said at least one protective layer and said at least one additional layer seal together and enclose said padding layer and said printed circuit board; wherein said at least one protective layer is configured to contact a wearer's skin, said at least one protective layer is configured for at least one of body electrical sensing, acoustic sensing, temperature sensing, collecting body fluids, electro-dermal activity, and piezoelectric sensing; and
   a power source coupled to said printed circuit board.

2. The device according to claim 1, wherein said printed circuit board comprises at least one electronic component built into at least one of a flexible substrate, a semi-rigid substrate and a rigid substrate.

3. The device according to claim 1, wherein said at least one additional layer is selected from the group consisting of a textile non-conductive layer, an acoustic/mesh layer, an insulating layer, heat dissipating layer and the like.

4. The device according to claim 1, wherein said at least one additional layer is selected from the group consisting of a heat dissipating layer, an acoustic layer, a membrane layer, a piezoelectric layer, an air channel layer, a fluid tray layer, a valve layer, an acoustic lens layer, an adhesive layer and a conductive fabric layer.

5. The device according to claim 1 wherein said physiological measurements and biometric measurements are selected from the group consisting of electrocardiogram, heart rate, heart rate variability, heart rate recovery, respiratory rate, temperature, body position, respiration, activity, movement, and the like.

6. The device according to claim 5, wherein said printed circuit board comprises an integrated circuit configured to process said physiological measurements and biometric measurements and wirelessly transmit said physiological measurements and biometric measurements to another device selected from the group consisting of a computer, a mobile phone, a recording device and the like.

7. A garment having a wearable monitoring device comprising:
   the wearable monitoring device coupled to said garment, wherein said wearable monitoring device comprises a printed circuit board having a first side and a second side opposite the first side, said printed circuit board is configured to couple to at least one sensor, said at least one sensor comprising a conductive layer configured to contact a wearer's skin; wherein said printed circuit board comprises an integrated circuit configured to process physiological measurements and biometric measurements and wirelessly transmit said physiological measurements and biometric measurements to another device selected from the group consisting of a computer, a mobile phone, a smart watch, a recording device and the like;
   a conductive pad coupled to said printed circuit board; and
   at least one soft-based module coupled to said wearable monitoring device and said garment, said at least one soft-based module configured to monitor a physiological condition through inputs of said physiological measurements and biometric measurements, said at least one soft-based module configured attachable to any garment or fabric, wherein said at least one soft-based module is configured integrated with said at least one sensor and soft-based modules configured to make different physiological and biometric measurements for different disease, health or body states.

8. The garment according to claim 7, wherein said at least one soft-based module has a biopotential sensor that enables biopotential measurements such as electrocardiography, Electroencephalogram, Impedance Cardiography, Electromyography and the like.

9. The garment according to claim 7, wherein said garment has the shape of an adjustable bra extension or sensor fabric swatch made of fabric, elastic, lace material and the like that attaches to any existing design of a daily bra, brallete, sports bra, t-shirt bra, lingerie or similar top.

10. The garment according to claim 7, wherein said garment comprises complimentary hooks configured to activate said wearable monitoring device responsive to said complimentary hooks making electrical contact.

11. The garment according to claim 7, wherein the at least one soft-based module coupled to said wearable monitoring device and said garment comprises a long-term body monitoring system for different diseases or health states selected from the group consisting of Atrial Fibrillation, Heart Failure, Respiratory Disease, Kidney Disease, Menopause and early menopause, Hyperlipidemia, Cardio-Pregnancy, Gestational Diabetes, Pre-eclampsia, Cardio-oncology, Autoimmune disease, Polycystic Syndrome, Smoking, Hypertension, Genetic predisposal to heart disease, Elderly, Endometriosis, Septicemia, Screening for traditional and emerging risks of heart disease, Depression, Alzheimer's and the like.

12. The garment according to claim 7, wherein said at least one soft-based module comprises an I/O interactive sensor configured for touch and optical measurements and indications.

13. The garment according to claim 7, further comprising: a pad coupled to said garment proximate said at least one sensor.

14. The garment according to claim 7, wherein the garment is configured to fit over a torso of a wearer.

15. The garment according to claim 14, wherein said garment is selected from the group consisting of a bra cup, a bra, a brallete, a camisole top, a tee shirt, shorts, sock, pants, a hat and the like.

16. The garment according to claim 7, wherein said conductive pad comprises a track width greater than 150% of a wire diameter used in the printed circuit board.

17. The garment according to claim 16, wherein the conductive layer that contacts the wearer's skin comprises a conductive material selected from the group consisting of silverized thread, Stretch Conductive Fabric, Silver plated, high conductivity, Tin/copper coated, Cobalt alloy top coating, Silver (Ag), Ag/AgCl plated knitted fabric.

18. The garment according to claim 7, wherein said at least one soft-based module comprises:
a front layer coupled to a conductive tape, said front layer being configured to directly contact skin of a wearer;
a circuit layer coupled to said conductive tape opposite the front layer; and
a padding layer coupled to said circuit layer opposite said conductive tape, wherein said padding layer being configured to attach to said garment.

19. The garment according to claim 18, wherein said at least one soft-based module comprises:
an air channel layer coupled to said circuit layer proximate the front layer;
a fluid tray layer coupled to the air channel layer; and
a valve layer coupled to the fluid tray layer; wherein said air channel layer, fluid tray layer and valve layer are configured to make fluidic measurements.

20. The garment according to claim 18, wherein said at least one soft-based module comprises:
a piezo electric layer coupled between the front layer and the circuit layer; wherein said piezo electric layer is configured to make mechanical pressure measurements.

21. The garment according to claim 18, wherein said at least one soft-based module comprises:
at least one acoustic layer coupled between the front layer and the circuit layer, wherein the at least one acoustic layer is configured for sound measurements.

22. A garment having a wearable monitoring device comprising:
the wearable monitoring device coupled to said garment, wherein said wearable monitoring device comprises a printed circuit board having a first side and a second side opposite the first side, wherein said printed circuit board comprises an integrated circuit configured to process physiological measurements and biometric measurements and wirelessly transmit said physiological measurements and biometric measurements to another device selected from the group consisting of a computer, a mobile phone, a smart watch, a recording device and the like;
at least one soft-based module coupled to said wearable monitoring device, said at least one soft-based module comprises:
a front layer coupled to a conductive tape, said front layer being configured to directly contact skin of a wearer;
a circuit layer coupled to said conductive tape opposite the front layer; and
a padding layer coupled to said circuit layer opposite said conductive tape, wherein said padding layer being configured to attach to said garment.

23. The garment according to claim 22, wherein said at least one soft-based module is configured to monitor a physiological condition through inputs of said physiological measurements and biometric measurements.

24. The garment according to claim 22, wherein said at least one soft-based module is configured attachable to any garment or fabric wherein said at least one soft-based module is configured integrated with at least one sensor and soft-based modules configured to make different physiological and biometric measurements for different disease, health or body states.

* * * * *